(12) United States Patent
Izmailov et al.

(10) Patent No.: US 9,989,525 B2
(45) Date of Patent: Jun. 5, 2018

(54) DIFFRACTION BASED BIOSENSOR CONTAINING TWO DIFFRACTIVE GRATINGS

(71) Applicant: AXELA INC., Etobicoke (CA)

(72) Inventors: Alexandre Izmailov, Toronto (CA);
Paul Timothy Smith, Acton (CA)

(73) Assignee: AXELA INC., Etobicoke (CA)

( * ) Notice: Subject to any disclaimer, the term of this patent is extended or adjusted under 35 U.S.C. 154(b) by 407 days.

(21) Appl. No.: 13/837,488

(22) Filed: Mar. 15, 2013

(65) Prior Publication Data

US 2014/0271363 A1 Sep. 18, 2014

(51) Int. Cl.
| | |
|---|---|
| G01N 33/543 | (2006.01) |
| G01N 33/50 | (2006.01) |
| G01N 21/77 | (2006.01) |
| G01N 21/47 | (2006.01) |

(52) U.S. Cl.
CPC ... *G01N 33/54373* (2013.01); *G01N 21/7743* (2013.01); *G01N 33/5017* (2013.01); *G01N 21/4788* (2013.01); *G01N 2021/7763* (2013.01); *G01N 2021/7776* (2013.01)

(58) Field of Classification Search
CPC ......... G01N 33/54373; G01N 21/7743; G01N 33/5017; G01N 21/4788
See application file for complete search history.

(56) References Cited

U.S. PATENT DOCUMENTS

| | | | |
|---|---|---|---|
| 5,822,472 A | 10/1998 | Danielzik et al. | |
| 8,283,156 B2 | 10/2012 | Goh et al. | |
| 8,349,617 B2 | 1/2013 | Weiss et al. | |
| 2003/0138208 A1* | 7/2003 | Pawlak et al. | 385/37 |
| 2009/0180932 A1 | 7/2009 | Angeley | |
| 2011/0111487 A1 | 5/2011 | Goh et al. | |
| 2012/0170050 A1 | 7/2012 | Savran et al. | |

FOREIGN PATENT DOCUMENTS

WO 2007010469 1/2007

OTHER PUBLICATIONS

International Search Report, PCT/CA2014/050137, dated Jul. 8, 2014, 3 pages.
Written Opinion of the International Authority, PCT/CA2014/050137, dated Jun. 12, 2014, 5 pages.

* cited by examiner

*Primary Examiner* — Melanie Yu Brown
(74) *Attorney, Agent, or Firm* — Hill & Schumacher

(57) ABSTRACT

The present disclosure provides a diffraction based biosensor containing at least two diffraction gratings. The first grating is referred to as an in-coupling diffraction grating and the coherent light source (laser) is directed to illuminate the in-coupling grating, and the biosensor is configured such that a selected order of the light beam diffracted from the in-coupling diffraction grating illuminates a second biosensor grating coated with analyte-specific receptors which are selected to preferentially bind with analytes being tested for that may or may not be located in a sample being tested.

49 Claims, 9 Drawing Sheets

DIFFRACTION BASED BIOSENSOR CONTAINING TWO DIFFRACTIVE GRATINGS

FIELD

The present disclosure relates to a diffraction based biosensor containing two or more diffractive gratings.

BACKGROUND

One of the major advantages of a diffraction based biosensor that is used in a reflective mode is that it can be used with non-transparent and/or absorbing samples. A diffraction based biosensor represents a phase diffraction grating that typically has a relatively low diffractive efficiency in reflection for low angles of incidence. The diffractive efficiency improves significantly at the angle of incidence that is close to the angle of total internal reflection. Utilization of these angles represents a technical difficulty that can be overcome by the use of the light deflection element such as a prism, (see M. C. Goh, Method and apparatus for assay based on light diffraction, US 2011/0111487) or a diffraction grating.

SUMMARY

The present disclosure provides a diffraction based biosensor containing at least two diffraction gratings. The first grating is referred to as an in-coupling diffraction grating and the laser light beam is directed to illuminate the in-coupling grating, and the biosensor is configured such that a selected order of the light beam diffracted from the in-coupling diffraction grating illuminates the second grating. The second grating, referred to as a biosensor diffraction grating, is coated with analyte-specific receptors which are selected to preferentially bind with analytes being tested for that may or may not be located in a sample being tested.

A embodiment of a diffraction based biosensor, comprises:

a) a substrate, said substrate being optically transparent and having a thickness T and a refractive index n;

b) at least one in-coupling diffraction grating located in a first position on a first surface of said substrate, said in-coupling diffraction grating having a grating period d such that said in-coupling diffraction grating produces a pre-selected number of diffraction orders k when illuminated by a laser light source of wavelength $\lambda$ at an angle of incidence $\alpha$;

c) at least one biosensor diffraction grating comprised of a diffraction grating having a grating period $d_s$ and analyte specific receptors located thereon and located in a second position on a second surface of said substrate and located, for a given substrate thickness T, spaced laterally in a direction of dispersion of the in-coupling diffraction grating from said first position a distance X such that at least one diffraction order of light diffracted from said in-coupling diffraction grating illuminates said biosensor diffraction grating at an angle of incidence $\theta$; and d) wherein when any analyte in a fluid having a refractive index of in contact with said biosensor diffraction grating binds with said analyte specific receptors a change in intensity of light diffracted from said biosensor diffraction grating is induced indicating the presence of the analytes in the fluid.

Another embodiment of a diffraction based biosensor comprises a) a substrate, said substrate being optically transparent and having a thickness T and a refractive index n;

b) an in-coupling diffraction grating having a refractive index $n_1$ and a height $h_1$ located in a first position on said substrate, said in-coupling diffraction grating having a grating period $d_1$ selected such that the grating produces a pre-selected number of diffraction orders k when illuminated by a laser light source of wavelength $\lambda$;

c) at least one biosensor including at least one biosensor diffraction grating with a refractive index $n_2$ and a height $h_2$ located in a second position on said substrate, and for a given thickness T spaced laterally, in a direction of dispersion of the in-coupling diffraction grating from said first position, a selected distance X such that at least one diffraction order of light diffracted from said in-coupling diffraction grating illuminates said biosensor, said at least one biosensor diffraction grating having a grating period $d_s$ and having analyte-specific receptors located thereon; and d) wherein when any analyte in a fluid in contact with said biosensor binds with said analyte specific receptors a change in intensity of light diffracted from the biosensor is induced indicating the presence of the analytes in the fluid.

Biosensor systems may be constructed using the above-mentioned diffraction-based biosensors, which includes a laser light source configured with the biosensor to illuminate the in-coupling diffraction grating, and a detector which is configured to receive a selected diffracted order of the light beam. The biosensor diffraction grating may be enclosed in a flow cell for flowing sample over the biosensor diffraction grating having the analyte specific receptors located thereon.

A further understanding of the functional and advantageous aspects of the disclosure can be realized by reference to the following detailed description and drawings.

BRIEF DESCRIPTION OF THE DRAWINGS AND TABLES

Embodiments will now be described, by way of example only, with reference to the drawings, in which.

Figure 5:
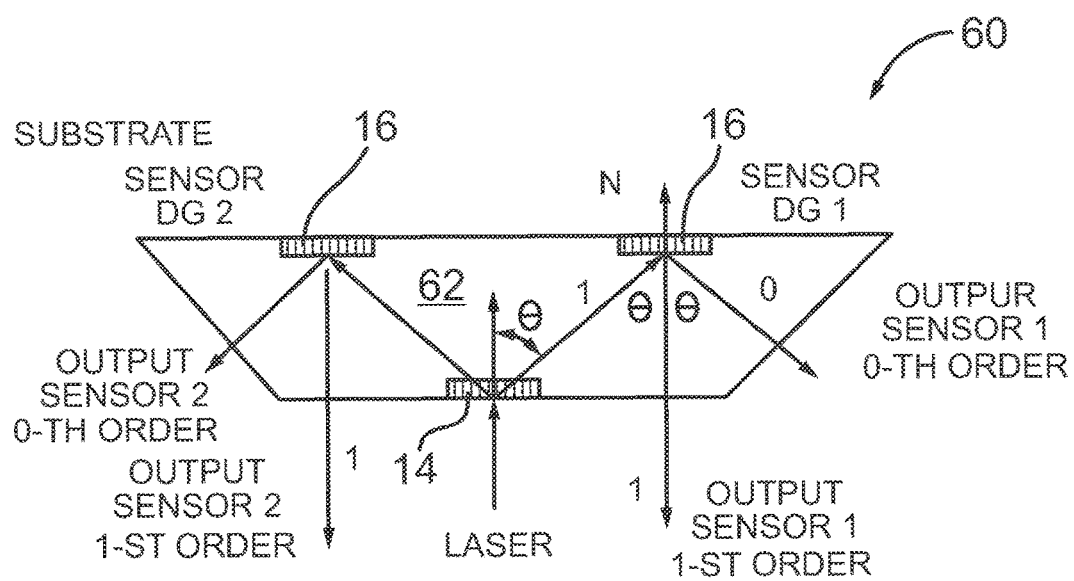
FIG. 5 shows variation of the embodiment of FIG. 4 in which the substrate is configured such that the $0^{th}$ and $1^{st}$ order light beams diffracted from the biosensor diffraction grating exit the substrate through substrate surfaces perpendicular to the respective exiting surfaces such that both diffracted beams can be utilized.
Figure 5A:
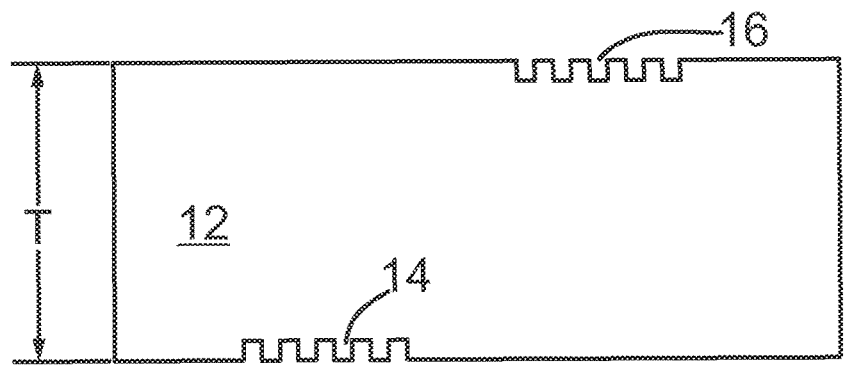
Figure 5B:
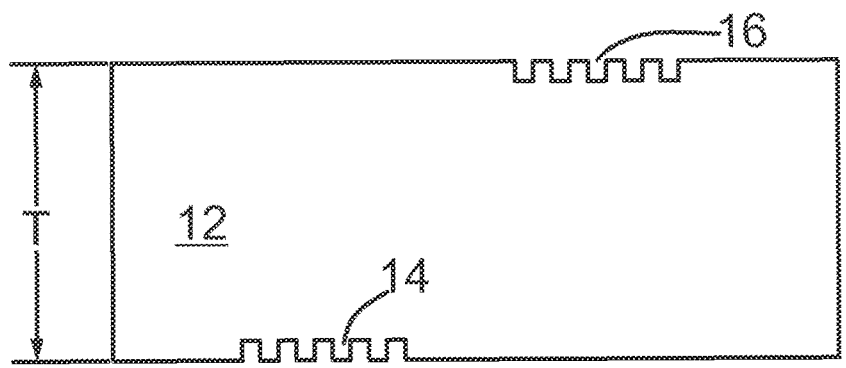
Figure 5C:
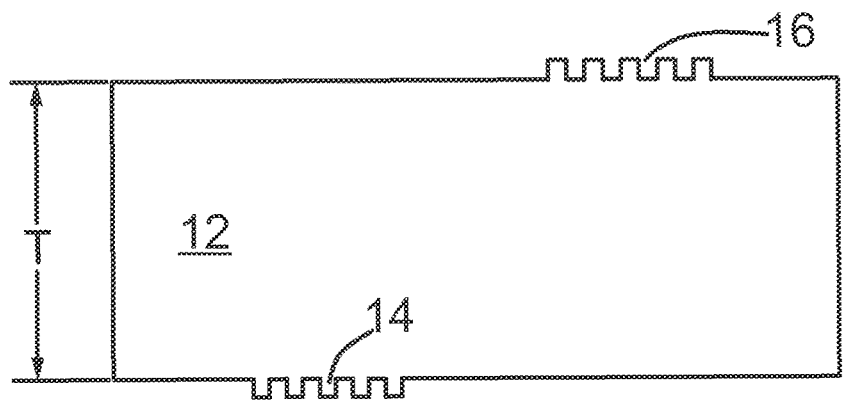
Figure 5D:
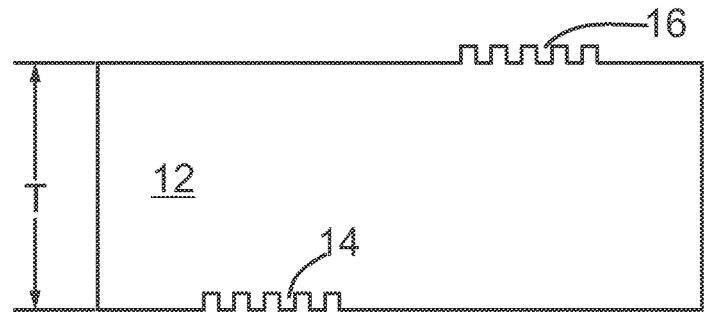

FIGS. 5a to 5d show different embodiments with the in-coupling grating and the biosensor grating configured in different ways, both gratings formed on of the substrate surface as in FIG. 5a, both gratings located in recesses in the substrate surface as in FIG. 5b, both gratings molded directly into the substrate surfaces as in FIG. 5c, one grating formed on top of the substrate surface and the other molded into the surface as in FIG. 5d.

Figure 5E:
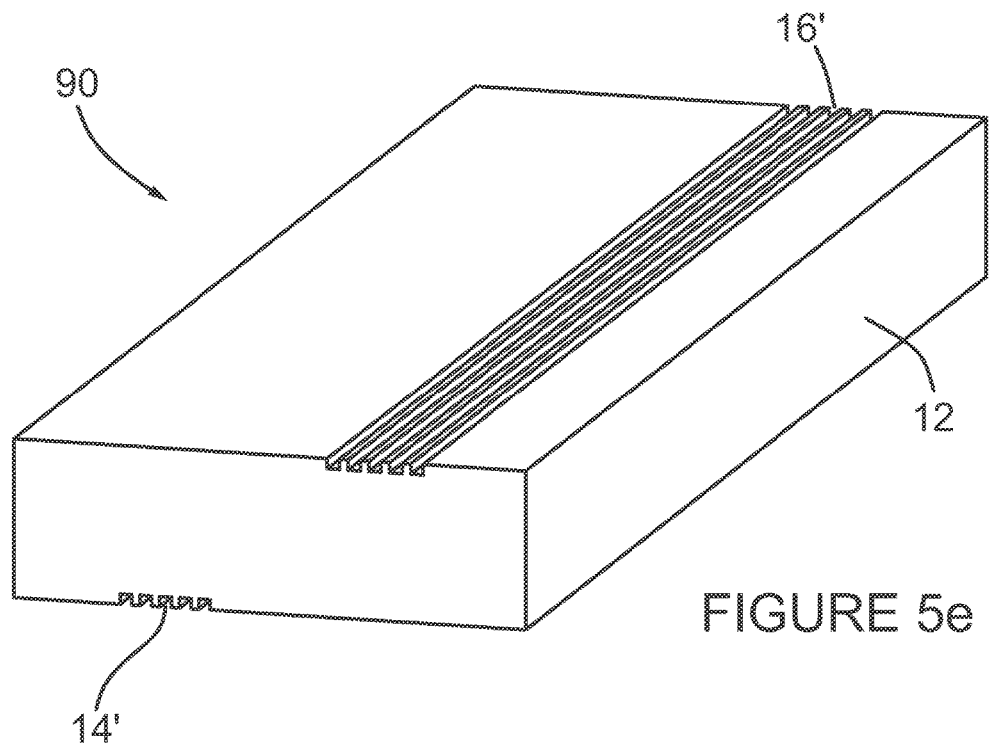

FIG. 5e shows and embodiment of a biosensor in which the in-coupling grating and the biosensor diffraction grating are elongate continuous gratings along the length of the substrate.

Figure 5F:
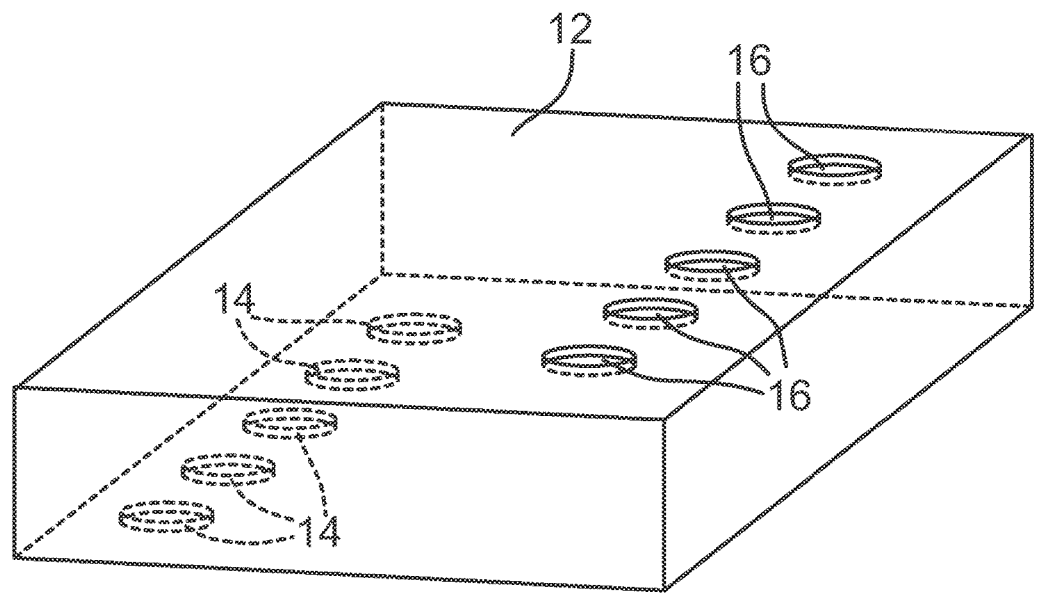

FIG. 5f shows and embodiment of a biosensor containing a plurality of in-coupling gratings and a plurality of biosensor diffraction gratings in a paired relationship spaced along the substrate which can be interrogated sequentially by one laser beam or simultaneously by several lasers.

Figure 5G:
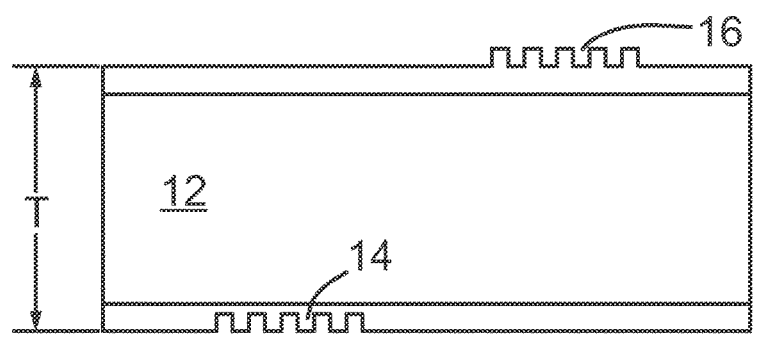

FIG. 5g shows another embodiment in which the grating 14 and/or grating 16 is created in an optically clear polymer film deposited on the surface of the substrate. This embodiment can be reduced to practice by depositing a photosensitive polymer on the surface with a consecutive photo lithography step creating a grating. One of the examples of such polymer film may be avidin.

Figure 6:
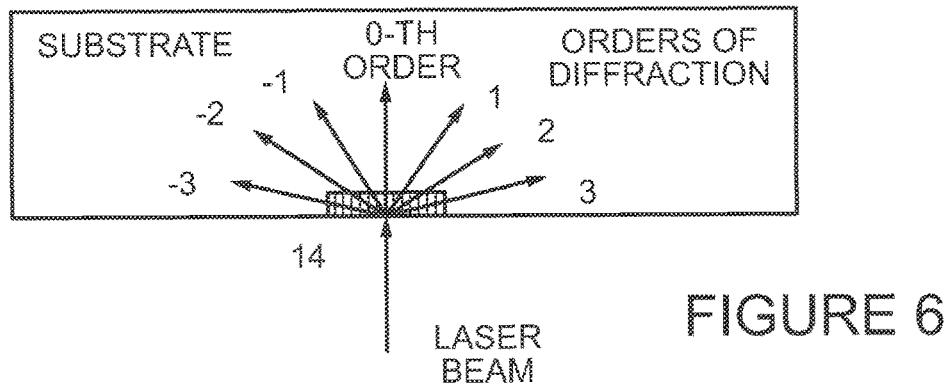

FIG. 6 shows that for in-coupling diffraction gratings having a large grating period multiple diffraction order are produced by the diffraction grating.

Figure 7:
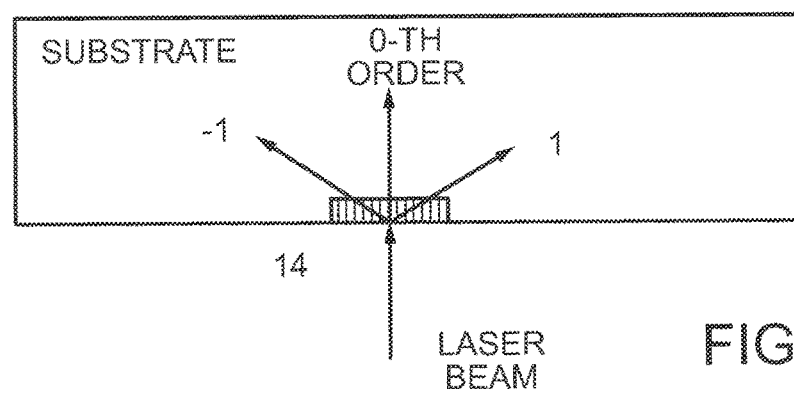

FIG. 7 shows that for in-coupling diffraction gratings having a small grating period fewer diffraction orders are produced by the diffraction grating compared to large period gratings of FIG. 6.

Figure 8:
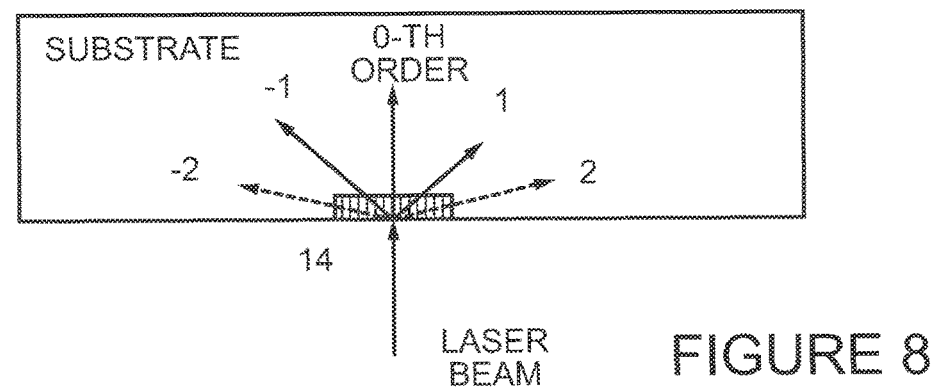

FIG. 8 shows a diffraction grating having rectangular grooves and other properties selected such that the diffracted light contains only the 1-st and 2-nd diffraction orders and that the intensity of the second order beams for a phase grating with rectangular groove is low compared to the first order, while theoretically it should be 0, but practically it is very low.

Figure 9:
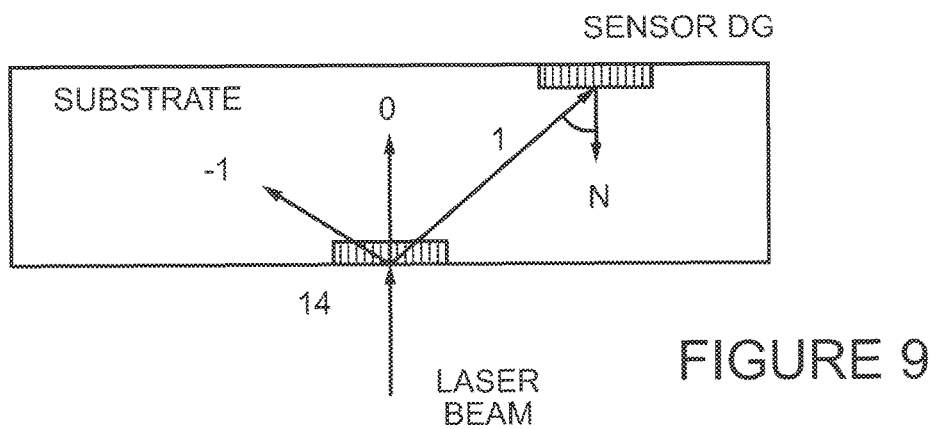

FIG. 9 shows a configuration of the present biosensor wherein selection of the period of the in-coupling diffraction grating is imposed by a required angle of incidence for the sensor diffraction grating as the angle of diffraction ψ produced by the in-coupling diffraction grating equals to the angle of incidence for the sensor diffraction grating.

Figure 10:
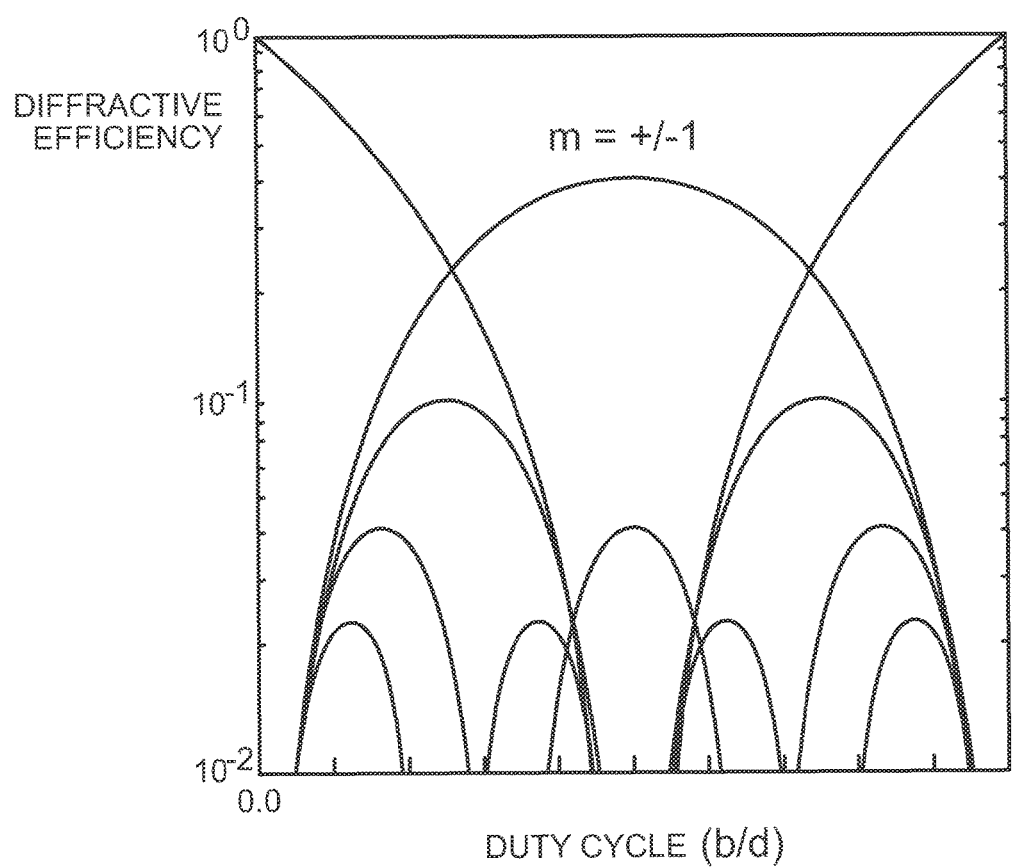

FIG. 10 shows plots of diffractive efficiency as a function of the grating duty cycle, see J. E. Harvey, Fundamentals of Applied Optics (OSE 5203), Diffraction Gratings, University of Central Florida, 2010).

Figure 11:
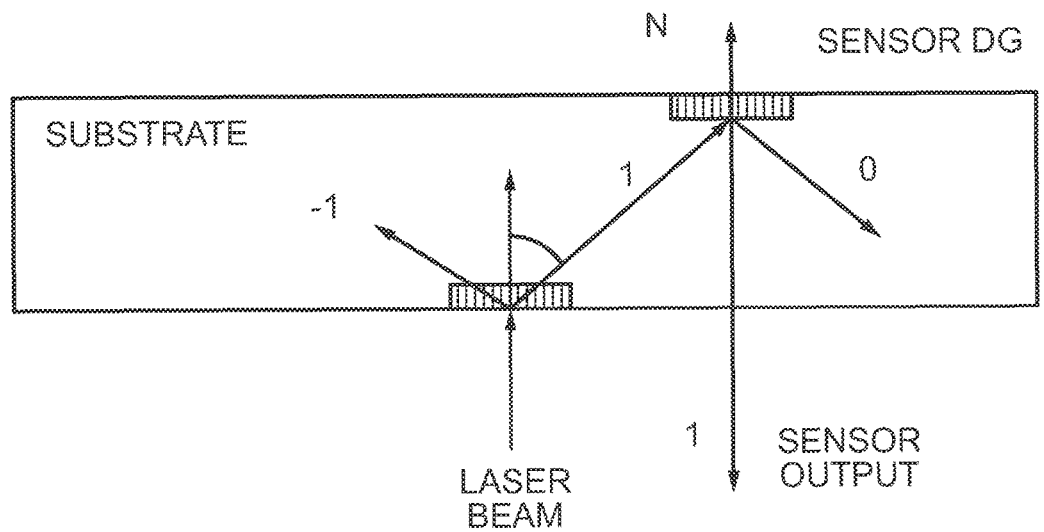
Figure 12:
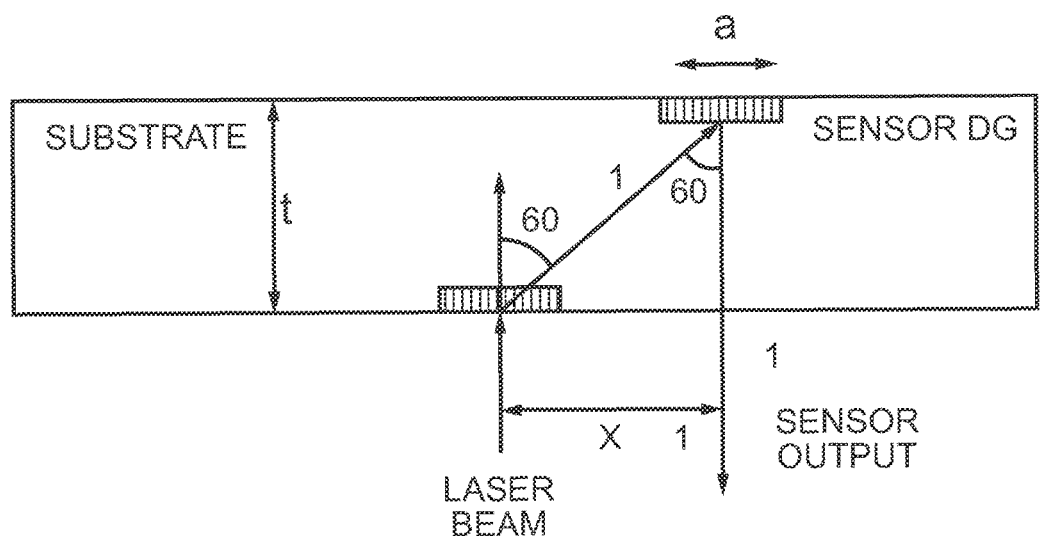

FIG. 11 shows a sensor with the sensor grating period selected such that the 1st order of diffraction propagates normally to the surface of the sensor FIG. 12 shows the relative position of the in-coupling and the sensor diffraction spots having grating properties selected to give an angle of incidence of 60° and the $1^{st}$ order beam diffracted from the biosensor grating to be perpendicular to the substrate surface that it exits through.

TABLE 1 tabulates the largest allowed period of the in-coupling diffraction grating producing a given number of diffraction orders.

TABLE 2 tabulates the period of the in-coupling diffraction grating for different required angles of incidence.

TABLE 3 tabulates the optimal depth of the in-coupling diffraction grating for a given set of grating parameters.

TABLE 4 tabulates the relative displacement of the in-coupling and the biosensor grating spots for different angles of incidence and the thickness of the substrate of 2.0 mm.

DETAILED DESCRIPTION

Various embodiments and aspects of the disclosure will be described with reference to details discussed below. The following description and drawings are illustrative of the disclosure and are not to be construed as limiting the disclosure. The drawings are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps, or components are included. These terms are not to be interpreted to exclude the presence of other features, steps, or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures, or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

Unless defined otherwise, all technical and scientific terms used herein are intended to have the same meaning as commonly understood to one of ordinary skill in the art. Unless otherwise indicated, such as through context, as used herein, the following terms are intended to have the following meanings.

The present disclosure provides a diffraction based biosensor containing at least two diffraction gratings. The first grating is referred to as an in-coupling diffraction grating and the laser light beam is directed to illuminate the in-coupling grating, and the biosensor is configured such that a selected order of the light beam diffracted from the in-coupling diffraction grating illuminates the second grating. The second grating, referred to as a biosensor diffraction grating, is coated with analyte-specific receptors which are selected to preferentially bind with analytes being tested for that may or may not be located in a sample being tested. The methodology for producing this diffraction-based biosensor involves the following approach, first discussing the various physical configurations the biosensor may take, the types of materials, the parameters of the two different gratings and various systems based on the different configurations.

Physical Configurations

Figure 1A:
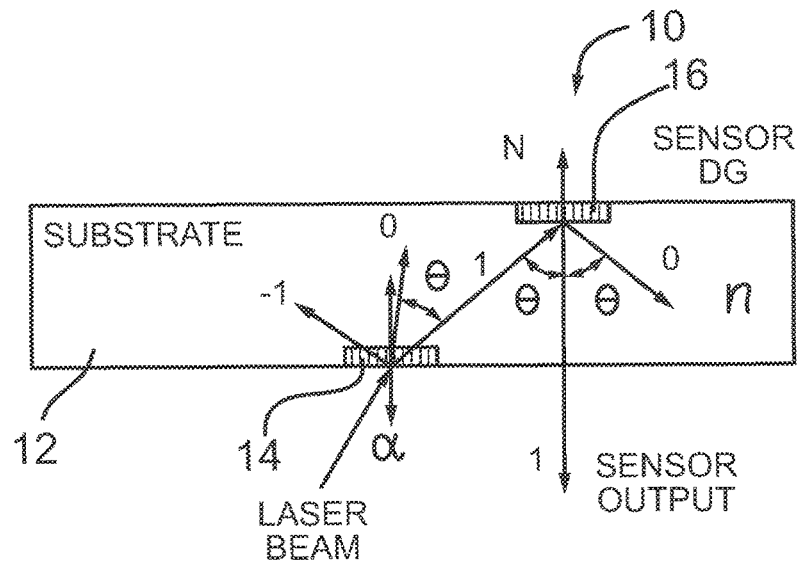
FIG. 1a shows an embodiment of a biosensor having an in-coupling diffraction grating and a biosensor diffraction grating on opposed planar surfaces of an optically transparent substrate.
Figure 1B:
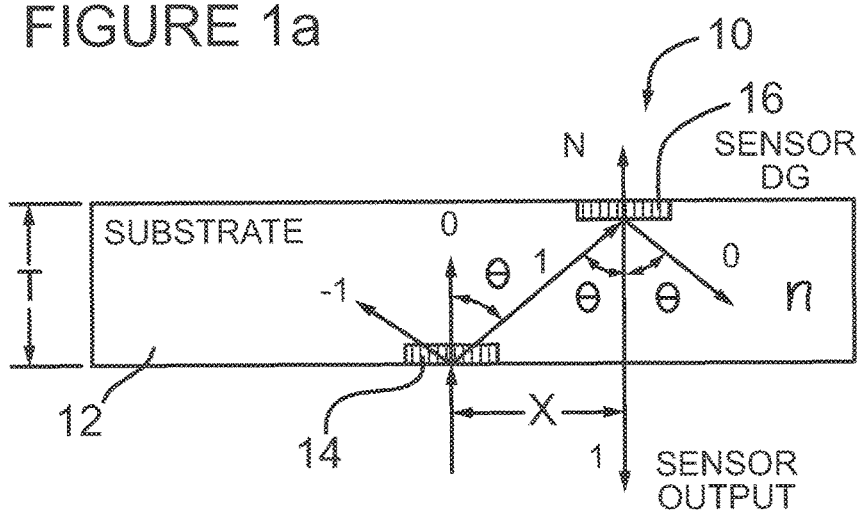
FIG. 1b shows the embodiment of FIG. 1a with the angle of incidence equal to 0 (normal incidence)

Referring to FIGS. 1a and 1b, an embodiment of the diffraction based biosensor is shown generally at 10 and includes an optically transparent substrate 12 having a refractive index n, an in-coupling diffraction grating 14 located on one surface of substrate 12 having a grating period d and, and a biosensor diffraction grating 16 located on the opposite or opposed side of substrate 12 having a grating period $d_s$ with gratings 14 and 16 being spaced laterally from each other a lateral distance X so that it this embodiment the in-coupling diffraction grating 14 is located on the surface opposite to the surface that is in contact with a biological sample on which biosensor grating 16 is located. In this embodiment the opposed surfaces containing the diffraction gratings 14 and 16 are separated by a thickness T. The gratings 14 and 16 are spaced apart by a lateral distance X. The thickness T, distance X and the grating period d are selected for a given wavelength λ and refractive index n such that the at least one diffraction order of light diffracted from the in-coupling diffraction grating is incident on the biosensor at an angle of incidence θ. FIG. 1a shows the zero-th order ($0^{th}$) and the first order ($1^{st}$) beams diffracted from in-coupling grating 14 with the sensor configured such that the first order diffracted beam illuminates the biosensor grating 16. FIG. 1b shows a configuration in which the parameters of the in-coupling grating 14 are chosen (as discussed below) to give an angle of incidence of 60° with the first order beam diffracted from biosensor grating 16 exiting substrate 12 perpendicular to the substrate surface.

Figure 2:
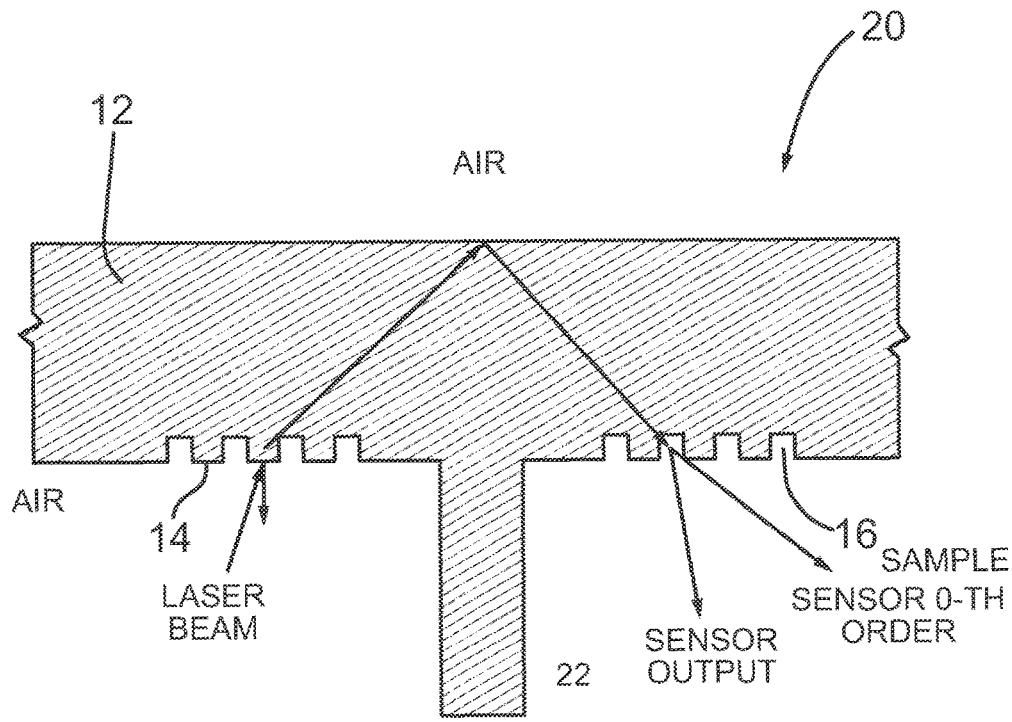
FIG. 2 shows another embodiment of a biosensor having the in-coupling diffraction grating and the biosensor diffraction on the same substrate surface for use in total internal reflection (TIR) mode.

Referring to FIG. 2, another embodiment is shown generally at 20 that uses total internal reflection on one of the surfaces of substrate 12 to redirect the diffracted beam produced by the in-coupling diffraction grating 14. In this embodiment, the in-coupling diffraction grating and the biosensor diffraction grating are located side-by-side on the same surface of the substrate, with a physical separation 22 located between the gratings 14 and 16 so that sample being investigated for the presence of analytes contacts only the biosensor diffraction grating and not the in-coupling diffraction grating. Thus, in this alternative configuration, gratings 14 and 16 are located on the same substrate surface and spaced apart by a distance X. The substrate has a thickness T, and the thickness T and selected distance X are selected for a given wavelength λ and refractive index n such that a selected diffraction order of light diffracted from in-coupling diffraction grating 14 illuminating biosensor grating 16 undergoes total internal reflection (TIR) at an interface formed by the opposed planar surface of substrate 12 and air and is directed to the biosensor grating 16 located adjacent to in-coupling diffraction grating 14.

Figure 3:
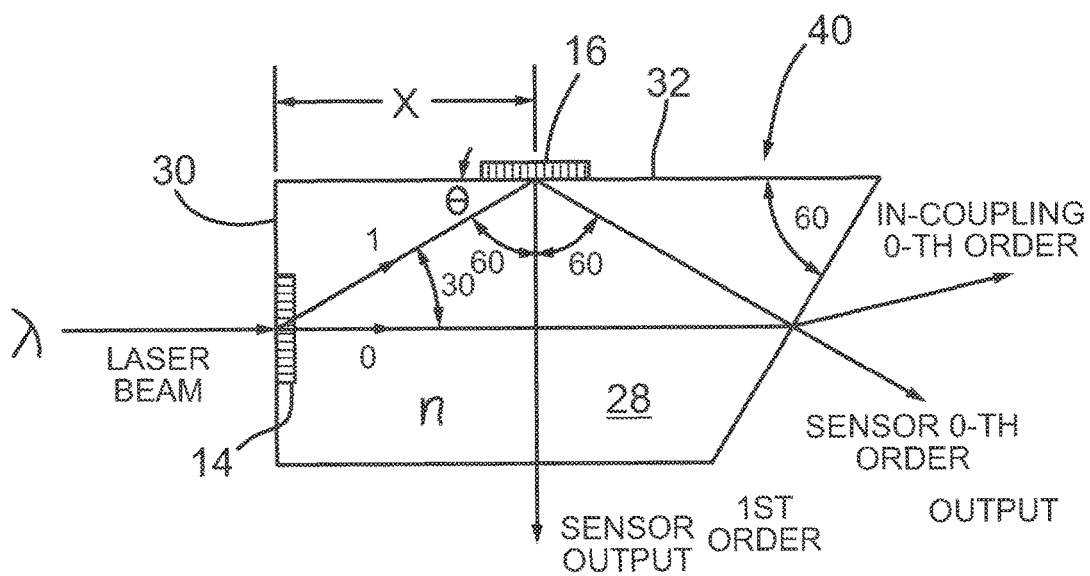
FIG. 3 shows another embodiment of a biosensor having the in-coupling diffraction grating and the biosensor diffraction on substrate surfaces perpendicular to each other.

Referring to FIG. 3, another alternative configuration for the diffraction based biosensor shown at 40 has the substrate 28 configured so that the in-coupling grating 14 located on a first planar surface 30 and the biosensor grating 16 located on a second planar surface 32 that is not parallel to the first planar surface and laterally spaced from grating 14 by a distance X. The distance X, the angle of incidence θ and the grating period d are selected for a given wavelength λ and refractive index n such that at least one diffraction order of light diffracted from the in-coupling diffraction grating 14 is incident on the biosensor grating 16. In an embodiment the second planar surface 32 is substantially perpendicular to the first surface 30 so that the gratings 14 and 16 are perpendicular to one another.

Figure 1C:
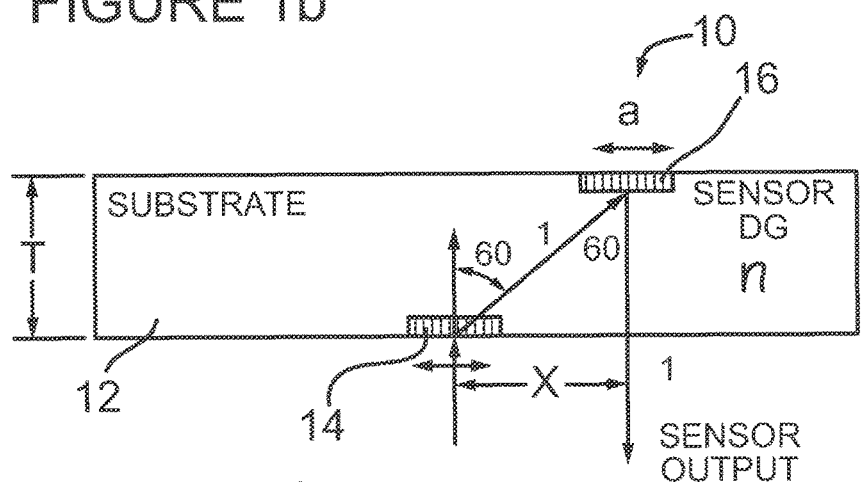
FIG. 1c shows the embodiment of FIG. 1b having the sensor configured for an angle of incidence of the beam diffracted from the in-coupling grating illuminating the biosensor grating to be at 60°.
Figure 4:
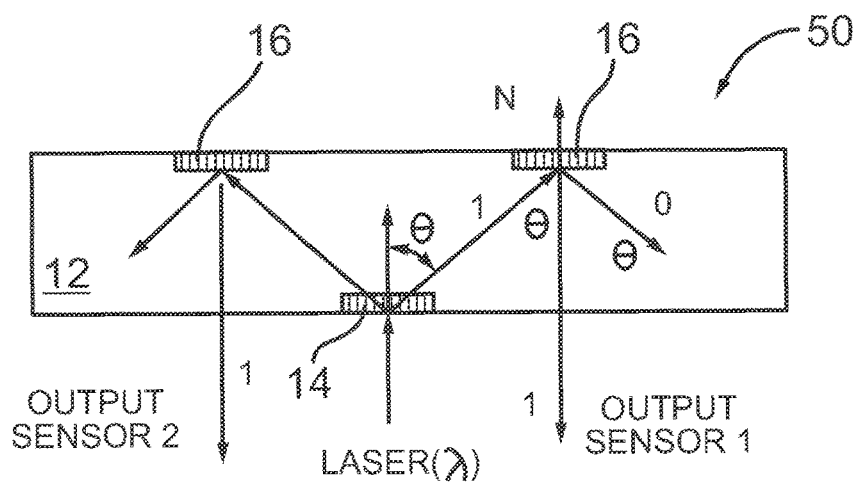
FIG. 4 shows an embodiment of a biosensor having an in-coupling diffraction grating and a biosensor diffraction grating on opposed planar surfaces of an optically transparent substrate but with two biosensor gratings spaced to be illuminated by the +/− first order diffracted light beams.

Referring to FIG. 4 another embodiment of a diffraction-based biosensor is shown at 50, constructed in accordance with the present disclosure, and includes two biosensor gratings 16, not just one as in FIG. 1. The biosensor 50 is configured so that the in-coupling diffraction grating 14 diffracts the plus and minus diffraction orders towards the biosensor gratings 16. In an embodiment, the biosensors 16 are configured, and oriented with respect to the detectors (not shown) so that the first order beams diffracted from gratings 16 are directed to the detectors.

FIG. 5 shows a similar embodiment at 60 with the substrate 62 having a trapezoidal shape so that both the zero-th ($0^{th}$) order diffracted beam and the first ($1^{st}$) order beam exit the substrate perpendicular to the surfaces they are exiting when it is desired to detect both beams, or reduce the impact of the scattered light originated by those orders of diffraction that are not exiting the optical part of the system. This type of approach allows for increasing the dynamic range of the system and allows for the selection of a direction of signal change with increase of the thickness of the layer of absorbed biological material on the surface of the biosensor grating 16.

In all the configurations disclosed above, the in-coupling diffraction grating 14 and the biosensor diffraction grating 16 may be located and formed on top of the substrate surface (see FIG. 5a), which may be preferred if the gratings 14 and 16 are made of materials different from the substrate 12 itself. Alternatively, gratings 14 and 16 may be located in recessed portions of either opposed surfaces (see FIG. 5b) or the same substrate side. The depth of each recessed portion may be equal to the height of the grating located in the recessed portion, or may be shallower or deeper than the height of the gratings. Alternatively, only one of the gratings may be formed in a recess and the other grating may be located on the surface of the substrate (not shown). In another embodiment, both gratings 14 and 16 may be molded directly into the substrate surfaces themselves (see FIG. 5c) which is preferred when the gratings and the substrate are all formed from the same polymer or plastic material.

Alternatively, one of the gratings could be molded in the plastic, such as grating 14 in FIG. 5d, while the other grating 16 may be made of a different material developed on the top of substrate 12.

FIG. 5g shows another embodiment in which the grating 14 and/or grating 16 is created in an optically clear polymer film deposited on the surface of the substrate. This embodiment can be reduced to practice by depositing a photosensitive polymer on the surface with a consecutive photo lithography step creating a grating. One of the examples of such polymer film may be avidin.

FIG. 5e shows another embodiment of the biosensor at 90 which uses an elongated continuous in-coupling diffraction grating 14' and an elongated continuous biosensor diffraction grating 16'. Alternatively only one grating may be elongate and continuous along substrate 12 and the other a series of gratings separated from each other spaced along substrate 12. Spaced along grating 16' (in the event it is the elongate grating), is a plurality of areas each having analyte-specific receptor spot. The analyte-specific receptors may all be the same type or they may be different for detecting different analytes of interest. The analyte-specific receptor spots are sufficiently separated from each other, and each diffracted beam of light incident on each analyte-specific receptor spot is configured to have a small enough spot size to ensure individual illumination of each of the localized analyte-specific receptor spots independent of all other biosensors.

FIG. 5f shows another embodiment at 100 wherein the in-coupling diffraction grating 14 is two or more in-coupling diffraction gratings 14 and biosensor diffraction grating 16 is two or more biosensor diffraction gratings 16, each of two or more in-coupling diffraction gratings 14 are paired with an associated one of the two or more biosensor diffraction gratings 16 to give two or more pairs, each of the two or more in-coupling diffraction gratings 14 being spaced sufficiently far from each other and each of the two or more biosensor diffraction gratings 16 being spaced sufficiently far from each other so that a laser beam illuminating one of the in-coupling diffraction gratings 14 illuminates only its paired biosensor diffraction grating 16 and no other.

The most practical approach is to form both gratings within the substrate polymer using a molding process. It is also possible emboss or print the gratings 14 and 16. The gratings 14 and 16 may be produced by covering of the surfaces of the substrate with a photo sensitive polymer and using photolithography to produce the gratings when the gratings are formed on the top surfaces of the substrates. This technique may also be used when the gratings 14 and 16 are formed in recesses in the substrate.

The secondary diffraction order(s) produced by the in-coupling diffraction grating may be used as a reference beam for normalization purposes. Alternatively, the multiple orders of diffraction produced by the in-coupling diffraction grating may be used for illumination of the radiation of two or more distinct biosensor gratings to increase the throughput of the system. The period, depth and the shape of the grooves of the biosensor diffraction grating are selected to provide the optimal sensitivity and dynamic range of the biosensor. The relative position of the in-coupling and the sensor diffraction gratings in the direction of dispersion of the in-coupling diffraction grating is selected such that a selected or pre-selected order of diffraction from the in-coupling diffraction grating illuminates the sensor diffraction grating.

In an embodiment, the period of the in-coupling diffraction grating is selected to limit number of diffraction orders (preferably to 0-th and +/−1st order). The period of the in-coupling diffraction grating and the angle of incidence of the laser beam onto the in-coupling diffraction grating is selected to provide a required angle of incidence of light onto a sensor diffraction grating.

As one of the implementations the 0-th order of diffraction produced by the sensor diffraction grating is used to increase system sensitivity to a change of the height of the sensor diffraction grating due to hybridization or absorption of molecules/species under test. In addition, one can simultaneously use 0-th order of diffraction and higher orders of diffraction produced by the sensor diffraction grating to increase the dynamic range of the system.

Materials

The two phase diffraction gratings 14 and 16 may be produced on one or more surfaces of the optically clear or transparent substrate 12, for example by being molded or etched into the plastic or polymer substrate. Optical transparency as used herein means transparent in the visible and/or near infrared spectrum or at least at the wavelength of the laser radiation that is used for illumination of the sensor. The substrate 12 and gratings 14 and 16 may be made of any one of a cyclo-olefin polymer, a polystyrene polymer, a polycarbonate polymer, polymethyl methacrylate, and a methyl methacrylate styrene copolymer.

Two particularly useful plastics are polystyrene polymer (PSE) and a cyclo-olefin polymer (COP). Both plastics are proven to be acceptable from the molding point of view. There are certain advantages from a manufacturing point of view to use COP. There is more experience in using PSE as a material for a diffraction based biosensor as this material has been used in the existing version of the sensor.

The substrate and the in-coupling diffraction grating and the diffraction grating having analyte-specific receptors located thereon may made of any one of cyclo-olefin polymer such as Zeonex, (for example, Zeonex E48R, Zeonex F52R) polystyrene, polycarbonate, Lexan (brand of polycarbonate), polymethyl methacrylate, methyl methacrylate styrene copolymer.

Any other plastic that is clear in the spectral range of the laser may be used in the present diffraction-based biosensor. This can include visible or near IR regions of spectrum. It is advantageous to use plastics with higher refractive indices in those embodiments that use the total internal reflection. The total internal reflection conditions are satisfied for a wider range of angles for higher refractive index of the plastic/polymer. A preferred, but not essential wavelength for the laser illuminating the sensor is 670 nm. It is noted that the refractive index of a material is wavelength dependent. The refractive indices for some of the plastics at the wavelength 670 nm include polycarbonate (PC) (n=1.57711); polystyrene (PS) (n=1.58425); Zeonex E548R (n=1.52676); Lexan 101 (n=1.58); and methyl methacrylate styrene copolymer (NAS) (n=1.55). Other polymers may be used as well, for example plastics containing nanoparticles as refractive index modifiers.

Example Implementation

An exemplary, non-limiting implementation using the configuration of FIG. 1b with the in-coupling grating 14 on one face of the substrate and the biosensor grating 16 on the opposed planar surface will now be discussed.

1. Selection of the Parameters of the in-Coupling Grating (IDG)

a) Grating Period

The period d of the in-coupling diffraction grating 14 defines the number of diffraction orders to which the original laser beam used to illuminate the grating 14 is split and the angle of diffraction for a given angle of incidence. The first is important because it changes the fraction of the laser power directed toward the sensor grating 16. The second is important because it defines the efficiency of the sensor diffraction grating 16. Selection of the grating period d based on the number of produced diffraction orders is determined by the angle of incidence of the incoming laser beam on the in-coupling grating 14 and the wavelength of the laser light.

It is assumed that the angle of incidence of the incoming laser beam=0 (the beam is perpendicular to the surface), and that the wavelength of laser radiation is 670 nm (0.67 um). Advantages of using normal incidence of light onto the in-coupling diffraction grating 14 are to: a) minimize the impact of shadowing; b) simplify optical coupling of the laser light; and c) simplify sensor design.

A non-normal incidence of light is also possible resulting in larger angle of incidence onto the sensor diffraction grating for a given period of the in-coupling diffraction grating.

For a large grating period d, multiple diffraction orders are produced by the in-coupling diffraction grating (IDG) 14. This is shown in FIG. 6.

The size of both diffraction gratings 14 and 16, their relative position on the substrate 12, the thickness of the substrate and the parameters of the in-coupling diffraction grating 14 are selected so that one of the diffraction orders produced by the laser beam illuminating the in-coupling diffraction grating illuminates the sensor diffraction grating spaced laterally from the in-coupling grating. The period, depth and the shape of the grooves of the in-coupling diffraction grating are selected to provide the optimal in-coupling of the laser beam diffracted from the in-coupling grating towards the biosensor grating.

In order to reduce the number of diffraction orders to +1/−1 (see FIG. 7) the period of the in-coupling diffraction grating shall comply with the following condition:

Sin θ=kλ/dn>1 for k>1 where θ is the angle of diffraction, k is the order of diffraction, λ is the wavelength of illuminating laser source, d is period of the diffraction grating and n is the refractive index of the substrate 12. This condition can be re-written as:

$$\frac{2\lambda}{dn} > 1 \text{ or } d < 2\lambda/n$$

Table 1 shows the largest allowed period of the in-coupling grating 14 producing a given number of diffraction orders. For the selected wavelength λ and refractive index n of the plastic the grating period shall not exceed 0.85 um if the requirement is to produce only the first order. In practice this condition can be relaxed if necessary (from the molding point of view) because for the ideal square-wave phase diffraction grating the intensity of the second order is supposed to be 0. This means that the period of the diffraction grating shall not exceed 1.27 um. This scenario is shown in FIG. 8.

TABLE 1

| Number of Diffraction Orders | Largest Allowed Grating Period, um |
|---|---|
| 1 | 0.85 |
| 2 | 1.27 |
| 3 | 1.69 |
| 4 | 2.11 |
| 5 | 2.54 |
| 6 | 2.96 |
| 7 | 3.38 |

The second criteria for selection of the period of the in-coupling diffraction grating is imposed by a required angle of incidence for the sensor diffraction grating as the angle of diffraction ψ produced by the in-coupling diffraction grating equals to the angle of incidence for the sensor diffraction grating (see FIG. 9). Making the assumption: Angle of incidence θ=60 degrees, then the required period of the diffraction grating can be calculated as:

d=λ/(n Sin θ)=0.5 um

For other angles of incidence on the sensor diffractive grating the required period of the in-coupling grating is shown in Table 2, which shows the period of the in-coupling diffraction grating 14 for different required angles of incidence.

TABLE 2

| Required Angle of Incidence | Grating Period |
|---|---|
| 30 | 0.85 |
| 40 | 0.66 |
| 50 | 0.55 |
| 55 | 0.52 |
| 60 | 0.49 |
| 65 | 0.47 |
| 70 | 0.45 | b) Grating Duty Cycle

As can be seen in FIG. 10, which shows diffractive efficiency as a function of the grating duty cycle, the optimal duty cycle of the grating is 0.5. This means that the width of the groove equals ½ of the grating period.

c) Grating Depth

The optimal depth of the in-coupling diffraction grating is the depth h that produces the phase shift Δ equal π.

$$\Delta = \frac{2\pi}{\lambda}(n-1)h = \pi$$

where Δ is the phase shift due to the difference in the path length of the rays propagating through the groove and the hill, λ is the wavelength of the laser light, n is the refractive index of the plastic used for the substrate, and h is the grating depth.

For the selected wavelength (670 nm) and substrate material (PSE) the optimal depth of the in-coupling diffraction grating 14 is 573 nm. The other possible depths are proportional to this value and can be selected depending on the requirements of the molding process. These values are listed in the Table 3. Note that if a plastic with lower refractive index (such as COP, for example) is selected as a substrate material, the optimal depth of the grating is increased (see Table 3).

TABLE 3

| Phase Shift in π | Optimal Grating Depth (PSE-Air), nm | Phase Shift in π | Optimal Grating Depth (COP-Air), nm |
|---|---|---|---|
| 1 | 573.4 | 1 | 644.2 |
| 2 | 1146.8 | 2 | 1146.8 |
| 3 | 1720.2 | 3 | 1720.2 |
| 4 | 2293.5 | 4 | 2293.5 |
| 5 | 2866.9 | 5 | 2866.9 |

2. Selection of the Parameters of the Sensor Grating a) The Grating Period

The biosensor 16 grating period is selected based on the possible limitations imposed by the functionalization process. It is advantageous to keep the same period as in the in-coupling diffraction grating 14. In this case—1st order of diffraction propagates normally to the surface of the sensor (see FIG. 11). This simplifies the system design, especially for miniaturized or integrated versions of the system.

b) The Initial Grating Depth

The initial depth of the biosensor diffraction grating 16 is selected to allow: a) functionalization of the top part ("hills") of the grooved area of the diffraction grating; b) to offset the optical signal and shift the grating thickness response curve to the range of maximum sensitivity range; and c) to choose positive or negative response of the system to changing thickness of the grating due to hybridization or absorption of molecules/species under test.

3. Selection of the Substrate Thickness

The first (and the major) limitation in selection of the thickness T of a substrate to be used for the sensor design is defined by the requirement that the 0-th order of the in-coupling grating 14 (propagating in the same direction as the straight laser beam for the normal incidence of laser light) shall be separated from the first order at the surface of the biosensor diffraction grating 16.

The second limitation is imposed by the molding process in embodiments in which the gratings are produced directly in the substrate using the substrate material for the gratings. A reasonable thickness of the sensor substrate when molding is used to produce the gratings currently is ~2 mm. Other methods of making gratings are available, including photolithography, laser etching, e-beam etching, etc. They may add additional limitations to the substrate thickness. Utilization of different methods of making of the diffractive gratings does not change the essence of performance of a sensor based on the proposed design.

4. Selection of the Relative Position of the in-Coupling and the Sensor Diffraction Grating.

In a non-limiting example of the selection of the relative positions of the in-coupling grating 14 and the biosensor grating 16, several assumptions may be made, including 1) assume the laser beam illuminating grating 14 is at normal incidence on the in-coupling grating 14, 2) select a substrate thickness is t=2.0 mm, 3) parameters of both gratings 14 and 16 are selected so that the angle of incidence on the sensor DG is 60 degrees, and 4) the spot size is a=2 mm (diameter). Referring to FIG. 12, based on these parameters, the lateral separation of gratings 14 and 16 is given by:

$$X = 2 \times \mathrm{Tan}(60) = 3.49 \text{ mm}$$

The spacing between the edges of the two spots in this case is 3 0.49−2.0=1.49 mm. this spacing can be reduced if a laser spot size is ~0.1 mm is used. The displacement of the center of the sensor spot from the center of the in-coupling grating 14 spot in the direction of dispersion for other angles of incidence (that can be required if the grating period cannot be kept at 0.5 um level) can be found in the Table 4. For angles of incidence below 60 degrees it is recommended to increase the substrate thickness to 3.0 mm (if this thickness is acceptable from the molding point of view).

TABLE 4

| Angle of Incidence, degrees | Lateral Shift, mm |
|---|---|
| 30 | 1.15 |
| 40 | 1.68 |
| 50 | 2.38 |
| 55 | 2.86 |
| 60 | 3.46 |
| 65 | 4.29 |
| 70 | 5.49 |

5. Orientation of the Grooves in Both Gratings

The suggested orientation of the grooves in both diffraction gratings is parallel to the direction of flow. Different orientations may be considered if it is necessary to increase the angle of incidence on the sensor DG with a given period of the in-coupling grating. A drawback of this approach is more complex arrangement of the sensing optics.

6. Selection of the Laser Wavelength

The wavelength of the laser light is considered to be 670 nm. It can be shifted to the near IR region (780 nm, for example) if the molding process require larger grating periods.

7. Laser Power

The theoretical limit of the in-coupling efficiency for the rectangular phase grating is ~40%. This may require increase of the laser power ~2-3 fold compared to the existing system if the same level of output signals is required.

Thus, based on the above design considerations, a non-limiting exemplary design of the sensor using gratings 14 and 16 on opposed surfaces of substrate 12 includes:
a) The laser wavelength=670 nm
b) The laser power=3-5 mW
c) Plastic substrate 12 is PSE
d) The spot size of both diffraction gratings=2 mm
e) The laser beam size=0.2 mm
f) The lateral spacing between the in-coupling and the sensor spots=3.5 mm
g) The diffraction grating period=0.5 um
h) Duty cycle=1
i) The depth of the In-coupling diffraction grating=210 nm
j) The direction of grooves—parallel to the flow when coupled with a flow cell.

It will be appreciated that while the above non-limiting example implementation is for the embodiment of FIG. 1*b* with the gratings 14 and 16 on opposed planar substrate surfaces, it will be appreciated that the same principles apply for the embodiments of FIG. 2 (total internal reflection) and FIG. 3, with gratings 14 and 16 on substrate surfaces essentially perpendicular to each other.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A diffraction based biosensor, comprising:
a) a substrate, said substrate being optically transparent and having a thickness T and a refractive index n;
b) at least one in-coupling diffraction grating located in a first position on a first surface of said substrate, said in-coupling diffraction grating having a grating period d such that said in-coupling diffraction grating produces a pre-selected number of diffraction orders k when illuminated by a laser light source of wavelength λ at an angle of incidence α;
c) at least one biosensor diffraction grating comprised of a diffraction grating having a grating period $d_s$ and analyte specific receptors located thereon and located in a second position on a second surface of said substrate and located, for a given substrate thickness T, spaced laterally in a direction of dispersion of the in-coupling diffraction grating from said first position a distance X such that at least one diffraction order of light diffracted from said in-coupling diffraction grating illuminates said biosensor diffraction grating at an angle of incidence θ; and
d) wherein when any analyte in a fluid having a refractive index $n_f$ in contact with said biosensor diffraction grating binds with said analyte specific receptors a change in intensity of light diffracted from said biosensor diffraction grating is induced indicating the presence of the analytes in the fluid.

2. The diffraction based biosensor according to claim 1 wherein said in-coupling diffraction grating has a grating depth h selected to satisfy a phase shift being equal to $\pi$ given by a relationship $$\Delta=(2\pi/\lambda)(n-1)h=\pi$$

where $\Delta$ is phase shift due to a difference in the path length of light rays propagating through a trough and a crest of said in-coupling grating.

3. The diffraction based biosensor according to claim 1 wherein said biosensor diffraction grating has an initial grating depth $h_s$ selected to allow a) functionalization of the top part of the grooved area of the diffraction grating; b) to offset the optical signal and shift the grating thickness response curve to the range of maximum sensitivity range; and c) to choose positive or negative response of the system to changing thickness of the grating due to hybridization or absorption of molecules/species under test.

4. The diffraction based biosensor according to claim 1, wherein said substrate has a first planar surface and an opposing second planar surface separated from said first surface by a thickness T, and the first and the second side surfaces connecting said planar surfaces and wherein said first position is located on said first planar surface and said second position is located on said second planar surface, and wherein said thickness T, said distance X and said grating period d for a given wavelength $\lambda$ and refractive index n are such that said at least one diffraction order of light diffracted from said in-coupling diffraction grating is incident on said biosensor diffraction grating at said angle $\theta$.

5. The diffraction based biosensor according to claim 4, wherein said substrate, said in-coupling diffraction grating and said diffraction grating having analyte-specific receptors located thereon are made of any one of a cyclo-olefin polymer, a polystyrene polymer, a polycarbonate polymer, polymethyl methacrylate, and a methyl methacrylate styrene copolymer.

6. The diffraction based biosensor according to claim 4, wherein said in-coupling diffraction grating has a grating depth h selected to satisfy a phase shift being equal to $\pi$ given by a relationship $$\Delta=(2\pi/\lambda)(n-1)h=\pi$$

where $\Delta$ is phase shift due to a difference in the path length of light rays propagating through a trough and a crest of said in-coupling grating.

7. The diffraction based biosensor according to claim 1 wherein said first and second surfaces are the same surface of the substrate.

8. The diffraction based biosensor according to claim 1 wherein said first and second surfaces are different surfaces of the substrate.

9. The diffraction based biosensor according to claim 1, wherein said substrate is an optically transparent plastic.

10. The diffraction based biosensor according to claim 9, wherein said optically transparent plastic is transparent in the visible and near infrared spectrum.

11. The diffraction based biosensor according to 1 wherein said substrate and said in-coupling diffraction grating and the diffraction grating having analyte-specific receptors located thereon are made of any one of a cyclo-olefin polymer, a polystyrene polymer, a polycarbonate polymer, polymethyl methacrylate, and a methyl methacrylate styrene copolymer.

12. The diffraction based biosensor according to claim 1, wherein said grating period d is selected to reduce the number of diffraction orders k produced by said in-coupling diffraction grating and thereby increase a fraction of laser power directed into the pre-selected number of diffraction orders k.

13. The diffraction based biosensor according to claim 1, wherein said grating period d is selected to reduce the number of diffraction orders k produced by said in-coupling diffraction grating to substantially the positive and negative first orders.

14. The diffraction based biosensor according to claim 1, wherein said grating period $d_s$ is selected to reduce the number of diffraction orders k produced by said biosensor diffraction grating and thereby increase a fraction of laser power directed into the pre-selected number of diffraction orders k.

15. The diffraction based biosensor according to claim 1, wherein said grating period $d_s$ is selected to reduce the number of diffraction orders k produced by said biosensor diffraction grating to substantially the positive and negative first orders.

16. The diffraction based biosensor according to claim 1, wherein said diffraction grating having analyte-specific receptors located thereon has a rectangular cross section shaped grooves.

17. The diffraction based biosensor according to claim 16, wherein said diffraction grating has a duty cycle of 0.5.

18. The diffraction based biosensor according to claim 16, wherein said diffraction grating is a superposition of two or more gratings with each of said two or more gratings having the same period but different duty cycles.

19. The diffraction based biosensor according to claim 1, wherein said in-coupling diffraction grating and said diffraction grating having analyte-specific receptors located thereon are both part of said substrate itself.

20. The diffraction based biosensor according to claim 1, wherein said angle $\theta$ of incidence of the laser radiation onto the said biosensor diffraction grating is greater than or equal to the angle corresponding to the conditions of the total internal reflection at the interface of the biosensor diffraction grating with the analyte.

21. The diffraction based biosensor according to claim 1, wherein said diffraction grating having analyte-specific receptors located thereon is made of a material different from the substrate material.

22. The diffraction based biosensor according to claim 21, wherein said diffraction grating having analyte-specific receptors located thereon is made of a photosensitive polymer.

23. The diffraction based biosensor according to claim 22, wherein said photosensitive polymer is avidin.

24. The diffraction based biosensor according to claim 1, wherein said in-coupling diffraction grating and said diffraction grating having analyte-specific receptors located thereon are both made of materials different from the substrate material at said first and second positions respectively.

25. The diffraction based biosensor according to claim 1, wherein one of said in-coupling diffraction grating and said diffraction grating having analyte-specific receptors located thereon is part of the substrate itself and the other is made of a material different from the substrate material.

26. The diffraction based biosensor according to claim 1, wherein said substrate includes a flow channel, said biosensor diffraction grating being located in said flow channel along which a fluid being analyzed for a presence of said analytes is flowed over said biosensor diffraction grating.

27. The diffraction based biosensor according to claim 1, wherein said grating period d is selected to reduce the number of diffraction orders k produced by the in-coupling diffraction grating to positive and negative first orders beams, and wherein said second position is located such that it is illuminated by either the positive or negative first order diffraction beam.

28. The diffraction based biosensor according to claim 27, wherein said biosensor diffraction grating is a first biosensor diffraction grating, and including a second biosensor diffraction grating located in a third position on said second planar surface and located such that either said negative or positive first order diffraction beam is incident thereupon, said third biosensor diffraction grating having substantially the same structure as the first biosensor diffraction grating.

29. The diffraction based biosensor according to claim 28, wherein the signal obtained from said second biosensor diffraction grating is used as a reference signal.

30. The diffraction based biosensor according to claim 1, wherein said substrate is an optically transparent polymer which is transparent in the visible and near infrared spectrum.

31. The diffraction based biosensor according to claim 1, wherein said period d is selected for a given wavelength $\lambda$ and refractive index n to give said angle of incidence $\theta$ between the beam diffracted from the in-coupling diffraction grating to the biosensor diffraction grating such that a first order beam of light diffracted from said biosensor diffraction grating propagates through, and out of, said substrate perpendicular to said first planar surface, and wherein said thickness T and said selected distance X are selected so that the light of a selected diffraction order diffracted from said in-coupling diffraction grating illuminates said biosensor diffraction grating at said angle of incidence $\theta$.

32. The diffraction based biosensor according to claim 1, wherein said angle of incidence $\alpha$ for the in-coupling diffraction grating is selected so that for given period d of said in-coupling grating and a given period of said biosensor diffraction grating $d_s$, said angle of incidence $\theta$ of light onto said sensor diffraction grating is such that a selected diffraction order produced by the biosensor diffraction grating propagates normally to said first surface of said substrate.

33. The diffraction based biosensor according to claim 1, wherein the second planar surface is not parallel to said first planar surface, and wherein said first position is located on said first planar surface and said second position is located on said second planar surface, said selected distance X, said angle of incidence $\theta$ and said grating period d are selected for a given wavelength $\lambda$ and refractive index n such that said at least one diffraction order of light diffracted from said in-coupling diffraction grating is incident on said biosensor diffraction grating.

34. The diffraction based biosensor according to claim 33, wherein said second planar surface is substantially perpendicular to said first surface.

35. The diffraction based biosensor according to claim 33, wherein said first side surface is slanted so that the angle of incidence $\beta$ onto said first side surface of the diffraction order of the laser beam diffracted on to the biosensor is in the range between 0 and 45 degrees.

36. The diffraction based biosensor according to claim 35, wherein the angle $\beta$ is substantially 0 degrees.

37. The diffraction based biosensor according to claim 1, wherein said wavelength $\lambda$ is 670 nm.

38. The diffraction based biosensor according to claim 1, wherein said at least one in-coupling diffraction grating is two or more in-coupling diffraction gratings and said at least one biosensor diffraction grating is two or more biosensor diffraction gratings, each of said two or more in-coupling diffraction gratings being paired with an associated one of said two or more biosensor diffraction gratings to give two or more pairs, each of said two or more in-coupling diffraction gratings being spaced sufficiently far from each other and each of said two or more biosensor diffraction gratings being spaced sufficiently far from each other so that a laser beam illuminating one of said in-coupling diffraction gratings illuminates only its paired biosensor diffraction grating and no other.

39. The diffraction based biosensor according to claim 38, wherein each of said two or more biosensor diffraction gratings have analyte-specific receptors located thereon which is different from the analyte-specific receptors on the remaining biosensor diffraction gratings.

40. The diffraction based biosensor according to claim 39, wherein number of said pairs is between 2 and 64.

41. The diffraction based biosensor according to claim 1, wherein one or both of said at least one in-coupling diffraction grating and said at least one biosensor diffraction grating includes an elongated continuous diffraction grating extending along a length of said substrate and a plurality of localized analyte-specific receptor spots formed on, and spaced from each other, along said elongated continuous diffraction grating, each analyte-specific receptor spot including analyte-specific receptors being different from analyte-specific receptors in all other analyte-specific receptor spots, said analyte-specific receptor spots being sufficiently separated from each other, and each diffracted beam of light incident on each analyte-specific receptor spot configured to have a small enough spot size to ensure individual illumination of each of said localized analyte-specific receptor spots independent of all other biosensors.

42. The diffraction based biosensor according to claim 41, wherein said localized analyte-specific receptor spots are illuminated sequentially by diffracted light originating from one laser.

43. The diffraction based biosensor according to claim 41, wherein said localized analyte-specific receptor spots are illuminated by diffracted light beams originating from a single laser through a beam splitter providing multiple beamlets that are redirected to the locations of the in-coupling grating corresponding to the positions of said analyte-specific receptor spots.

44. The diffraction based biosensor according to claim 41, wherein said localized analyte-specific receptor spots are illuminated by diffracted light beams originating from a single laser with a beam deflector providing consecutive illumination of the locations of the in-coupling grating corresponding to the positions of the said localized spots with analyte-specific receptors.

45. A biosensor system for detection of analytes in a sample, comprising
said diffraction based biosensor according to claim 1,
a laser source configured to emit a laser beam at said wavelength $\lambda$, said wavelength $\lambda$ being in the optical and near infrared spectrum, said laser source and said diffraction based biosensor being mounted with respect to each other such that said laser beam is incident on said in-coupling diffraction grating at angle $\alpha$ and a preselected order of light diffracted by said in-coupling grating impinges on said biosensor diffraction grating; and
a detector, said detector and said diffraction based biosensor being mounted with respect to each other such that said detector is positioned for detecting a preselected order of light diffracted by said at least one biosensor diffraction grating.

46. A diffraction based biosensor, comprising:
a) a substrate, said substrate being optically transparent and having a thickness T and a refractive index n;
b) an in-coupling diffraction grating having a refractive index $n_1$ and a height $h_1$ located in a first position on a surface of said substrate, said in-coupling diffraction grating having a grating period $d_1$ such that the grating produces a pre-selected number of diffraction orders k when illuminated by a laser light source of wavelength $\lambda$;
c) at least one biosensor diffraction grating each comprising a diffraction grating having a grating period $d_s$, said diffraction grating having a grating period $d_s$, a refractive index $n_2$ and a height $h_2$ and being located in a second position on a surface of said substrate, and for a given thickness T spaced laterally, in a direction of dispersion of the in-coupling diffraction grating from said first position, a distance X such that at least one diffraction order of light diffracted from said in-coupling diffraction grating illuminates said biosensor diffraction grating; and
d) wherein when any analyte in a fluid in contact with said biosensor diffraction grating binds with said analyte specific receptors a change in intensity of light diffracted from the biosensor diffraction grating is induced indicating the presence of the analytes in the fluid.

47. The diffraction based biosensor according to claim 46, wherein said in-coupling diffraction grating and said at one biosensor diffraction grating are located on top of opposed surfaces of said substrate.

48. The diffraction based biosensor according to claim 46, wherein one of said in-coupling diffraction grating and said at least one biosensor diffraction grating are located in a recessed portion of said surface with a depth of said recessed portion being equal to the height of the grating located in said recessed portion, and the other diffraction grating being located on top of the opposed surface.

49. The diffraction based biosensor according to claim 46, wherein said in-coupling diffraction grating and said at least one biosensor diffraction grating are located in recessed portions of said opposed surfaces with a depth of each recessed portion being equal to the height of the grating located in said recessed portion.

* * * * *